(12) United States Patent
Zhu et al.

(10) Patent No.: US 8,889,947 B2
(45) Date of Patent: Nov. 18, 2014

(54) HYBRID RICE SEED PRODUCTION METHOD

(75) Inventors: Xudong Zhu, Hangzhou (CN); Yuexing Wang, Hangzhou (CN); Shen Ni, Hangzhou (CN); Hongqi Chen, Hangzhou (CN)

(73) Assignee: China National Rice Research Institute, Hangzhou, Zhejiang Province (CN)

( * ) Notice: Subject to any disclaimer, the term of this patent is extended or adjusted under 35 U.S.C. 154(b) by 783 days.

(21) Appl. No.: 13/129,540

(22) PCT Filed: Jun. 18, 2009

(86) PCT No.: PCT/CN2009/072327
§ 371 (c)(1),
(2), (4) Date: May 16, 2011

(87) PCT Pub. No.: WO2010/096975
PCT Pub. Date: Sep. 2, 2010

(65) Prior Publication Data
US 2011/0232247 A1 Sep. 29, 2011

(30) Foreign Application Priority Data

Feb. 26, 2009 (CN) .......................... 2009 1 0096400
Mar. 19, 2009 (CN) .......................... 2009 1 0300956

(51) Int. Cl.
*A01H 1/00* (2006.01)
*A01H 1/02* (2006.01)
*A01H 5/00* (2006.01)
*C12N 5/04* (2006.01)
*A01H 5/10* (2006.01)

(52) U.S. Cl.
CPC ... *A01H 5/10* (2013.01); *A01H 1/00* (2013.01)
USPC .......................... 800/260; 800/320.2; 435/410

(58) Field of Classification Search
USPC ..................... 800/320.1, 260, 320.2; 435/410
See application file for complete search history.

(56) References Cited

FOREIGN PATENT DOCUMENTS

| CN | 1263701 | 8/2000 |
|---|---|---|
| CN | 101112180 | 1/2008 |
| CN | 101218889 | 7/2008 |

OTHER PUBLICATIONS

Zhu, et al., "Screening and Characterization of Mutants Induced from Zhoughua 11 (*Oryza sativa*L. subsp. *japonica*) by Irradiation", Chinese J Rice Sci, vol. 17, No. 3, Mar. 2003, pp. 205-210.
Gu, et al., "Screening and Identification of mutants induced from rice Zhonghua 11 (*Oryza sativa* L. subsp. *japonica*) by ethyl methane sulphonate (EMS)", Acta Agriculture Shanghai, vol. 21, No. 1, Feb. 2005, pp. 7-11.
Yu, et al., "Characterization and Genetic Studies on Dwarf Rice Mutant Xiaoxiang'ai with Small Grains", Hybrid Rice, vol. 22, No. 6, Jun. 2007, pp. 67-70.
Ma, et al., "Co-segregation Analysis Between T-DNA Tag and Character of Small Grain Dwarf Mutant in Rice", Chinese J Rice Sci, vol. 22, No. 6, 2008, pp. 571-577.
International Search Report issued in International Application No. PCT/CN2009/072327, mailed Dec. 3, 2009, 3 pages.

*Primary Examiner* — Medina A Ibrahim
(74) *Attorney, Agent, or Firm* — Hamre, Schumann, Mueller & Larson, P.C.

(57) ABSTRACT

The invention relates to a method for simplifying hybrid rice seed production procedure and improving the working efficiency of seed production. The method comprises the following steps: (1) breeding small grain CMS or GMS line and corresponding hybrid rice having characteristics of rice (*Oryza sativa*) ZH-sg (Zhonghua 11 small grain mutant) with the accession number of CGMCC No. 2741; (2) hybridizing the small grain CMS line with large grain or normal grain restorer line hybrid rice for seed producing; (3) carrying out mechanized seed production of mixing sowing and mixing harvesting by utilizing small grain CMS line hybrid rice; (4) seed cleaning and separation after mechanical harvest. The invention can save a large amount of seed production field, reduce the investment of labor force in seed production, simplify the operation procedure and reduce mechanical admixture, storage and transportation cost and buying cost of hybrid rice seeds for rice farmers.

11 Claims, 2 Drawing Sheets

A method for simplifying hybrid rice seed production procedure and improving the working efficiency of seed production, comprising the following steps:

HYBRID RICE SEED PRODUCTION METHOD

TECHNICAL FIELD

The invention belongs to the field of plant life science and particularly relates to the technical field of hybrid rice breeding.

BACKGROUND ART

The utilization of heterosis of crops must be premised on obtaining F1 hybrid seeds at low cost, so that a user can buy hybrid seeds and plant hybrid rice to obtain yield and benefits. Said hybrid seeds are produced by two parents having hereditary stability and different genotypes through sexual hybridization (hybrid seeds F1 has genotype heterozygosis and completely identical expressivity). Plant heterosis has universality, and whether the heterosis can be effectively utilized largely depends on the cost of hybrid seed production and the purchasing capacity of users. Hybrid rice has been widely popularized successfully for over 30 years in China, and in order to obtain higher yield potential of hybrid rice, improving the grain weight of rice is commonly used in present, which increases the seed quantity (weight) and therefore increases the seed buying cost.

Since heterosis utilization of hybrid rice is successfully realized in China in 1974, the method of interval sowing of male parent (restorer line) and female parent (CMS or GMS line) and respectively obtaining the male parent and the female parent has been used all long, which not only has complex operation technique but also increases the labor cost, and during seed production, the male parent which is higher than the female parent after gibberellin ($GA_3$) treatment for better cross pollination, the higher male parent is liable to lodging, and lodged plants or a minority of tiller ears are difficult to clear away in firstly harvest of male parent resulting in reduction of the purity of hybrids (mixed with a part of restorer line).

In the present hybrid seeds F1 production in China is according to period from seeding to heading between CMS or GMS line (female parent) and restorer line (male parent), interval sowing and interval or simultaneous transplanting are carried out, the male parent is immediately cut off after the completion of flowering, or the male parent is firstly cut off about 25 days after flowering (even the male parent is immediately cut off after the completion of flowering for preventing hybrid mixing with the male parent), and finally hybrid seeds of the female parent pollinated from restorer line are harvested after being grown. This hybrid rice production has been used for 35 years since 1974, and laborers for the seed production are more than common rice production by 3-4 laborers per mu (1 mu=0.067 Hectare) in merely interval sowing, interval or respectively transplanting of male and female parents and interval or respective harvest of the male and female parents.

In order to improve hybrid rice seed production efficiency, scientific researchers have done a lot of research, for example, the patent of China (CN200710070995) discloses a method for improving the efficiency of seed multiplication and production of hybrid rice by utilizing double-grain mutant, which improves the seed production efficiency by using double-grain mutant to improve CMS line; the patent CN99101907 discloses a hybrid rice seed production method, which improves the purity of seed production through chemical emasculation and weeding gene introduction. However, these methods are essentially different from the application.

A small grain mutant (ZH-sg, 1000-grain weight is about 20 g) obtained from r-ray mutagensis is under control of single recessive gene sg which has no bad effects on rice plant height, tillering capacity, photosynthetic capacity, spikelet fertility, grain shape, etc. The characteristic of small grain is controlled by single recessive gene sg, and hybrid seeds F1 produced by CMS or GMS line improved from the mutant are small grains. The small grain characteristic is unsuitable for improving yield potential of conventional rice seed production but completely feasible for the improvement of hybrid rice CMS or GMS line. Currently, there is not any report on utilizing small grain recessive mutation to improve CMS or GMS line, neither report nor invention on utilizing the difference of grain size to carry out mixed harvest and separating hybrid seeds from male parent according to the size of seeds by means of a mesh screen.

SUMMARY OF THE INVENTION

The object of the invention is to introduce small grain mutant gene sg into any type of CMS or GMS line of rice through sexual hybridization to merely minify seeds of the CMS or GMS line but not change the size of grains of hybrid rice, thereby reducing seed production area to improve the land utilization efficiency and reducing the seed cost of rice farmers to increase the income of the rice farmers. Meanwhile, mixed sowing of male parent (restorer line) and female parent (CMS or GMS line) in seed production simplifies the pressure of hybrid rice seed production, which at least eliminates separated removal of the male parent after the completion of cross pollination of rice so as to reduce the investment of labor by 1-2 laborers per mu (1 mu=0.067 Hectare) caused by separated removal of the male parent (namely, compared with separated remove of the male parent, the labor is reduced by 1-2 laborers per mu (1 mu=0.067 Hectare) of seed production field by combining with mechanical harvesting), so that the seed production cost is reduced, and the reduction of the cost reduces the buying cost of rice farmers and increases income of the rice farmers. More importantly, only when the mixing harvesting is realized will it be possible to realize mechanized production of hybrid rice seed production.

The invention is realized through the following technical solution:

BRIEF DESCRIPTION OF THE INVENTION

A method for simplifying hybrid rice seed production procedure and improving the working efficiency of seed production, comprising the following steps:

(1) breeding small grain cytoplasmic male sterile (CMS) or genic male sterile (GMS, such as photo- or thermal-sensitive genic male sterile) line hybrid rice having characteristics of rice (*Oryza sativa*) ZH-sg (Zhonghua 11 small grain mutant) CGMCC No. 2741;

(2) hybridizing the small grain CMS or GMS line hybrid rice obtained in step (1) with large grain or normal grain restorer line hybrid rice for seed producing.

Preferably, in the method according to the invention, in step (1) of breeding the small grain CMS or GMS line hybrid rice, hybrid rice having small grain gene sg mutant acting as donor parent is hybridized with three-line CMS maintainer line hybrid rice, two-line GMS line hybrid rice or other types of CMS line hybrid rice acting as receptor parent, and maintainer line or CMS or GMS line hybrid rice which stably carries mutated gene sg can be obtained through 5-7 generations of selection, wherein the hybrid rice having small grain gene sg mutant is rice (*Oryza sativa*) ZH-sg (Zhonghua 11 small grain mutant) which is deposited in CGMCC at Nov. 7, 2008, with the accession number of No. 2741.

Preferably, in the method according to the invention, the 1000-grain weight of said small grain CMS or GMS line hybrid rice is 19-21 g or lighter than that of large or normal grain CMS or GMS line hybrid rice by 25-45 percent. Generally, the 1000-grain weights of three-line CMS maintainer line hybrid rice, two-line GMS line hybrid rice or other types of CMS line receptor parent having normal to large grains are 26-30 g.

Preferably, in the method according to the invention, said three-line CMS line, two-line GMS line or other types of CMS line hybrid rice are selected from CMS line II-32A, Neixiang 2A, Tianfeng A, GMS line Guangzhan 63S conventional varieties/lines P13, NPB, etc.

Preferably, in the method according to the invention, in said 5-7 generations of selection, the separated individual carrying sg gene undergoes background selection of receptor parent by means of molecular marker technology, during the selection molecular marker takes the genotype of the receptor parent for reference to assists the selection. In the selection of individuals carrying sg gene, the individuals having more grains per ear than the receptor parent are selected, and the number of grains of the finally selected maintainer line or CMS line carrying sg gene is obviously larger than the receptor parent so as to compensate the miniaturization of grains and balance the yield level.

Preferably, in the method according to the invention, in the step (2) when the difference between the growth period of the small grain CMS or GMS line hybrid rice and the restorer line hybrid rice is shorter than 10 days, both are sown one after another or simultaneously sown together, and the restorer line hybrid rice is firstly transplanted and then the CMS line or GMS line hybrid rice is directly sown or both are transplanted together.

More preferably, in the method according to the invention, in the step (2) when the difference between the growth period of the small grain CMS or GMS line hybrid rice and the restorer line hybrid rice is shorter than 10 days, both are simultaneously sown together and transplanted together.

Preferably, in the method according to the invention, said restorer line hybrid rice is carried out by mixing sowing or direct sowing when the restorer line hybrid rice having the 1000-grain weight larger than 26 g.

Preferably, the method according to the invention further comprises the following steps:

(3) mixed harvesting, namely when hybrid seeds F1 produced by the small grain CMS or GMS line hybrid rice are fully grown, the hybrid seeds F1 and the restorer line seeds are harvested together; and (4) seed cleaning and separating, namely the hybrid seeds F1 and the restorer line seeds are separated by size.

Preferably, in the method according to the invention, the separation of the hybrid seed F1 from the restorer line seeds by size can be carried out via a proper mesh screen.

DETAILED DESCRIPTION OF THE INVENTION

Rice farmers buy hybrid seeds by kilogram (kg), essentially by number of hybrid seeds for a certain planting area. In terms of the same 1000 grains, different weight of each seed causes different final total weight. If the seeds of hybrid rice are small grains, and the hybrid rice produce large grains (or normal grains), the efficiency and the benefit can be improved to some extent.

The invention provides ZH-sg (Zhonghua 11 small grain mutant) with the accession number of No. 2741 and deposited in CGMCC (China General Microbiological Culture Collection Center) at Nov. 7, 2008, which is a small grain mutant (ZH-sg, 1000-grain weight is about 20 g) obtained from r-ray mutagensis and controlled by single recessive gene sg which has no bad effects on rice plant height, tillering capacity, photosynthetic capacity, spikelet fertility, grain shape, etc. Because the small grain characteristic is controlled by single recessive gene sg, and hybrid seeds F1 produced by CMS or GMS line improved from the mutant are small grains (because hybrid seed is controlled by the genotype of female parent, i.e., CMS or GMS line), if male parent is restorer line with 1000-grain weight of 26 g or heavier, mixed sowing even direct sowing, at least mixed harvesting (male parent and female parent) can be carried out, especially mechanized mixed harvesting can be carried out, mixed seeds after harvesting can be sorted by a proper mesh screen during commercial seed cleaning to separate hybrid seeds from male parent, that is because in the cleaning of hybrid seeds, small seeds (hybrid seeds produced by the female parent) with 1000-grain weight less than 20 g pass through the mesh screen, while normal seeds and large seeds (restorer line) can not pass through the mesh screen. Being controlled by single recessive gene, the small grain characteristic has no influence on the rice farmers' yield and the expression of hybrid rice.

The mutation characteristic can introduce small grain gene sg into any different material via sexual hybridization. If the small grain characteristic is introduced into three-line CMS line hybrid rice, two-rice GMS line hybrid rice or other types of CMS line hybrid rice via hybridization and backcross, the operation procedure of hybrid rice seed production is simplified and therefore the seed production efficiency of hybrid rice is improved. The small grain characteristic is unsuitable for the improvement of yield potential of conventional rice seed production but completely feasible for the improvement of CMS or GMS line of hybrid rice.

In order to compensate the decrease of yield caused by small grain, in the selection of individuals carrying sg gene, the individuals having more grains per ear than the receptor parent are selected, so that the number of grains of the finally selected maintainer line or CMS or GMS line carrying sg gene is obviously larger than the receptor parent. The yield of gramineous crop usually has three factors including number of productive ears of unit area, number of filled grain per ear and grain weight. Among the three factors the increase of the ratio of only one factor can possibly improve the yield. However, the increase of one factor generally decreases the other or other two factors in various degrees, and the increase of final yield is very limited. Therefore, if rice CMS or GMS line is improved by means of small grain mutant ZH-sg, the number of grains per ear or the number of tillering, namely the number of productive ears must be increased when the grain weight is reduced.

The small grain mutant sg can be used for improving nuclear-cytoplasmic interaction sterile three-line CMS line (A or B) as well as on the GMS line of photo (thermal)-sensitive genic male sterile line (S) induced by environment interaction and hybrid seeds produced by other ways (such as chemical emasculation).

The method of the invention generally comprises the following steps: (1) breeding small grain CMS or GMS line hybrid rice, for example, small grain mutant ZH-sg with 1000-grain weight of 19 g acting as female parent is hybridized with P13 with 1000-grain weight of 25 g, small grain individuals having small grain mutant gene sg are selected from F2' and is planted to become F3', the successive generations are of small grain type, and then the substantially stable small grain line is hybridized and backcrossed with three-line CMS line hybrid rice such as II-32A, and two-line GMS line hybrid rice such as Guangzhan 63S and the like to obtain three-line CMS line hybrid rice, two-line GMS line hybrid rice and other types of CMS line hybrid rice having ZH-sg small grain mutant characteristics;

(2) mixed sowing: the CMS or GMS line hybrid rice controlled by single recessive gene sg is used for seed production and matched with restorer line having normal or large grain and proper growth period, the male parent and the female parent are sown one after another or simultaneously, or the male parent is firstly transplanted and then the female parent is directly sown, thereby simplifying and saving labor compared with the present seed production; (3) mixed harvesting: there is no need to individually harvest the male parent after flowering of the male and the female parents, which is replace by mixed harvesting with a reaper; (4) separation with a mesh screen: in the procedure of cleaning harvested mixture of the male parent and the hybrid (F1) before packing, the small grain hybrid produced by CMS or GMS line is separated from large or normal grain restorer line by using a mesh screen to separate grains according to different 1000-grain weights, namely different sizes.

Specifically, said small grain CMS or GMS line hybrid rice breeding adopts the following methods:

(A). hybrid rice having small grain gene sg mutant acting as donor parent is hybridized with three-line CMS maintainer line hybrid rice, two-line GMS line hybrid rice or other types of CMS line hybrid rice acting as receptor parent to obtain hybrid F1', the hybrid F1' is planted to obtain F2' generation, when seeds produced by plants of F2' generation express the 1000-grain weight in the level of three-line CMS maintainer line hybrid rice, two-line GMS line hybrid rice or other types of CMS line hybrid rice, a quarter of individuals carrying the small grain gene sg are separated from the F2' generation, and the individuals carrying the sg gene are planted to become F3' generation which still is small grain, wherein said hybrid rice having small grain gene sg mutant is ZH-sg rice (*Oryza sativa*) which is deposited in CGMCC at Nov. 7, 2008, with the accession number of No. 2741; and (B) individuals carrying small grain gene sg and having similar appearance to the receptor parent are selected from F2' generation and backcrossed with the receptor parent or backcrossed according to the procedure of the step A, and in the case of a quarter of small grain individuals still can be separated after first backcross with BC1F2' generation and secondary backcross with BC2F2' generation, individuals having similar appearance to the receptor and smaller grains (namely carrying sg gene) are selected to obtain CMS line or homokaryotic maintainer line, or GMS line, hybrid rice which stably carries mutant gene sg and small grain characteristic after 5-7 generations of selections.

Seed cleaning is a necessary procedure after hybrid seed production in China, aiming to clean away straws, soil blocks, weed seeds and the like. China has been made a series of strict laws relating to the production and sale of crop seeds, and general hybrid rice after harvest needs to be cleaned, namely impurities such as straws, soil blocks, weed seeds and the like is removed by a screw screen (main way). In the present invention, the separation of hybrid seed F1 (small grain) from the male parent (large or normal grain) can be completed only by additionally providing a proper mesh screen on a cleaner. If using the current universal hybrid rice cleaner, mixed harvesting of the male parent and the female parent can be realized by separating the seeds with different sizes, thereby greatly simplifying the procedure of seed production.

The key of the present invention is small grain mutant (ZH-sg) being controlled by single recessive gene, contemporary seeds produced by F1 plants is controlled by female parent genotype to present small grains, while rice grains of hybrid F1 planted by farmers are controlled by male parent (restorer line) gene, so that the grains of hybrid F1 is normal in size so long as the gene of the male parent for controlling grains is normal. Contemporary hybrid seeds produced by small grain sterile parent are small grains and can be separated from large or normal grain male parent by a specific mesh screen, namely by a commonly used rice grain cleaner in China, and when mixed seeds (hybrid seeds F1 produced by CMS or GMS line+inbred seeds produced by restorer line) are cleaned by the mesh screen, so long as a specially designed mesh screen is mounted or replaced on the cleaner, hybrid seeds F1 and the inbred male parent seeds can be completely separated because small grains of hybrid seeds F1 can pass through meshes, and large grains of the inbred male parent seeds can not pass through the meshes.

The invention has the following advantages:

The invention is mainly applied to the hybrid seed production link of hybrid rice and can not affect hybrid rice production. The 1000-grain weight of mutant rice (*Oryza sativa*) ZH-sg (Zhonghua 11 small grain mutant) is 20 g (original parent of 24 g/1000 grains), while the 1000-grain weight of common rice CMS line such as "Jin 23A" (trade name) is 25 g, the heavier 1000-grain weight of rice such as "Neixiang 2A" (trade name) is 30 g. Provided the weight of the hybrid seeds F1 produced by one mu (1 mu=0.067 Hectare) of hybrid seed production field is 200 kg, the number of seeds of F1 generation with 1000-grain weights of 20 g, 25 g and 30 g are 10,000,000 grains, 8,000,000 grains and 6,660,000 grains, respectively. In China, farmers plant hybrid rice by one seedling per pit and then 15,000 seedlings per mu (1 mu=0.067 Hectare), and counting by sowing 20,000 F1 seeds per mu (1 mu=0.067 Hectare), said three hybrid seeds with the same weight and different 1000-grain weights can be planted for 500 mu, 400 mu and 333 mu, respectively. The amounts of seeds per mu of said hybrid seeds with different 1000-grain weights, converted into weights, are 400 g, 500 g and 600 g, respectively. If the prices of seeds (weight, kg) are same 16 Yuan/kg, the costs are 6.4 Yuan, 8.0 Yuan and 9.6 Yuan, respectively.

The 1000-grain weight of mutant ZH-sg (Zhonghua 11 small grain mutant) is 20 g (original parent of 24 g/1000 grains), while the 1000-grain weight of restorer line of China is more than 26 g. In the present invention, the hybrid seeds (small grain) can be separated from the male parent (large or normal grain) by replacing a proper mesh screen on the current common cleaner, mixed harvesting of male and female parents of hybrid rice can be realized by separating seeds with different sizes, thereby greatly simplifying the procedure of hybrid rice seed production.

Rice CMS or GMS lines carrying small grain gene being used for seed production can save a large amount of rice seed production field for country, reduce the investment of labor during seed production, simplify the operation procedure and reduce mechanical admixture, storage, transported amount and cost for seed companies, and reduce the buying cost of hybrid rice seeds for rice farmers.

BRIEF DESCRIPTION OF DRAWINGS

FIG. 3-1 and FIG. 3-2 are photos of mesh screens for cleaning seeds after rice seeds are harvested and dewatered, FIG. 3-1 is a round-hole mesh screen, and FIG. 3-2 is a strip-hole mesh screen.

DETAILED DESCRIPTION OF THE EMBODIMENTS

The invention is further specifically described by combining the following embodiments. It is to be understood that the invention is not limited by the following embodiments, and all equal replacements and/or changes are seen to fall within the scope of the invention.

In the invention, all devices, materials and the like are available on market or commonly used in the industry unless specified.

Embodiment 1

Breeding of Small Grain CMS Or GMS Line Hybrid Rice

Rice (*Oryza sativa*) ZH-sg (Zhonghua 11 small grain mutant) is taken as donor parent (the accession number of No. 2741, deposition date at Nov. 7, 2008) and is hybridized with main CMS or GMS lines for present hybrid rice seed production in China including II-32A (three-line CMS line with 1000-grain weight of 28 g), Neixiang 2A (three-line CMS line with 1000-grain weight of 30 g, Guangzhan 63S (two-line GMS line with 1000-grain weight of 28 g) and the like to improve the miniaturization of CMS line seeds.

Figure 1:
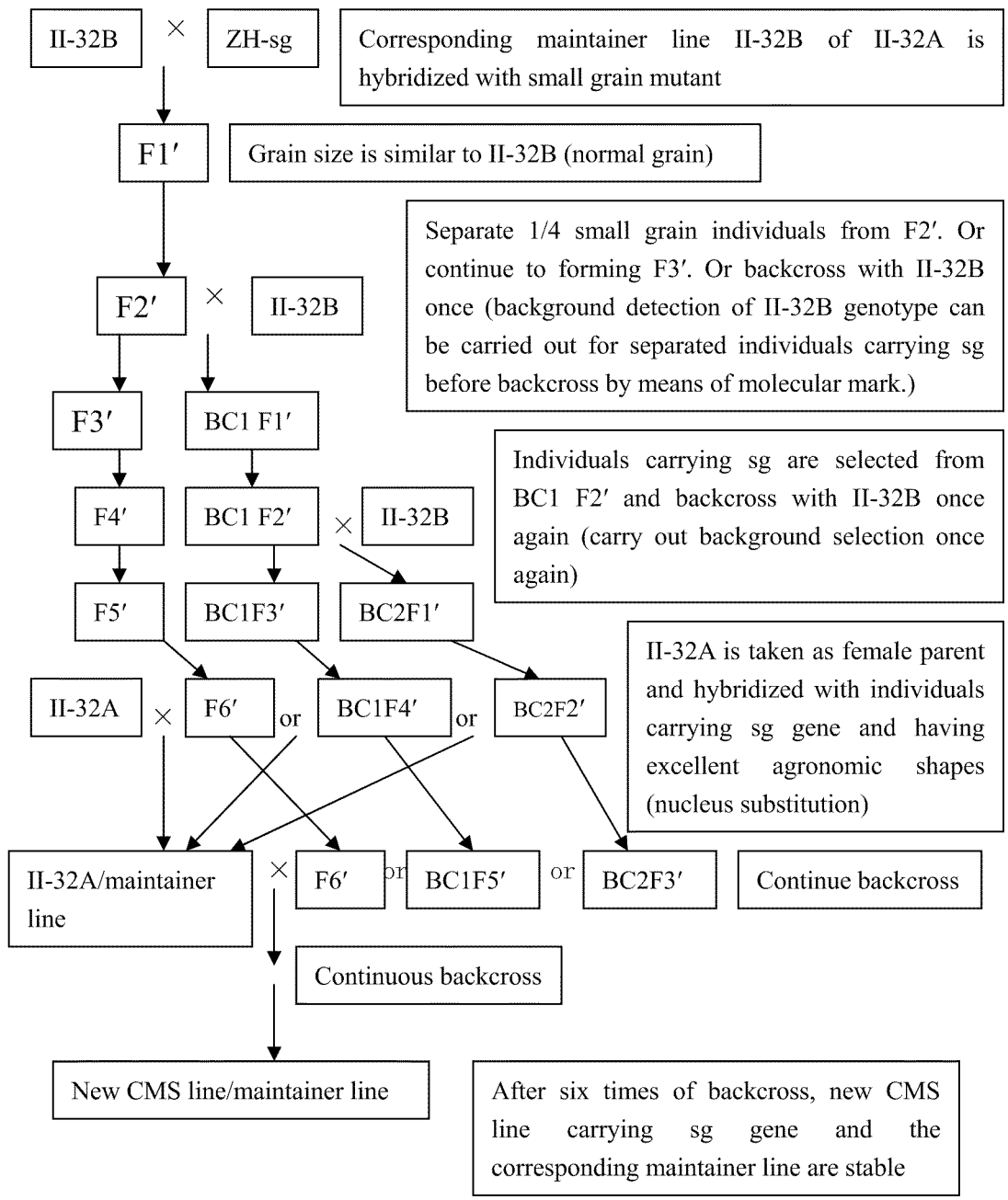
FIG. 1 is a flow diagram of embodiment 1.

The embodiment of the invention is herein described by combining FIG. 1, wherein small grain mutant ZH-sg acts as donor parent, and II-32A and corresponding maintainer line thereof of II-32B (receptor parent) are taken for example.

1. The corresponding maintainer line II-32B of II-32A is hybridized with small grain mutant ZH-sg to obtain F1' generation which is similar to II-32B (normal grain) in seed size, and F2' generation can be obtained by conventionally planting F1'.

2.1 A quarter of small grain individuals are separated from F2' and backcrossed with II-32B once to obtain BC1F1' generation. Before backcross, the separated individuals having sg undergoes background detection of II-32B by means of molecular marker technology, or the individuals which are similar to II-32B as much as possible in morphological characters are selected.

2.2 F3' generation is obtained by conventionally planting F2' and so on, F4' generation, F5' generation and F6' generation can be obtained.

3.1 If the backcross is carried out once, BC1F2' generation can be obtained by conventionally planting BC1F1' and so on, BC1F3' generation, BC1F4' generation and BC1F5' generation can be obtained.

3.2 individuals having sg gene can be selected from BC1F2' and are backcrossed with II-32B for the second time to obtain BC2F1' generation. In the backcross, background selection or similarity selection to II-32B is carried out again.

4. BC2F2' generation is obtained by conventionally planting BC2F1' and so on, BC2F3' generation is obtained.

5. II-32A is taken as female parent and hybridized with individuals carrying sg gene and having excellent agronomic shapes, namely F4'-F5', BC1F2'-BC1F3' and BC2F2', i.e. namely nucleus substitution. Then the individuals carrying sg gene and having excellent agronomic shapes are F5'-F6' generation, BC1F3'-F4' generation and BC2F3' generation. Such nucleus substitution hybridization needs to be carried out at least five times to obtain novel CMS line (A)/maintainer line (B) or GMS line carrying sg gene and having similar gene background to II-32. (Note: if the improvement is desired to be faster, lower generation such as F4' can be hybridized and backcrossed with II-32A for nucleus substitution, and there is no substantially difference in essence)

Figure 2:
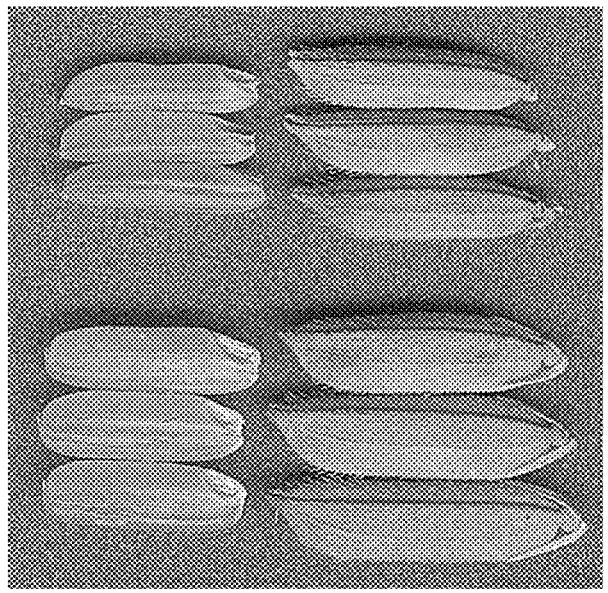
FIG. 2 shows maintainer line improved by small grain mutant (the upper part of the figure is maintainer line with 1000-grain weight of 20 g, the left part shows unpolished rice grains, and the right part shows rice grains. The maintainer line is hybridized with three-line CMS line hybrid rice for nucleus substitution to form corresponding CMS line), and restorer line hybrid rice grains which are common in present production (the lower part shows the restorer line with 1000-grain weight of 27 g, the left part shows unpolished rice grains, and the right part shows rice grains)

The novel CMS line/maintainer line or GMS line has the characteristics that the 1000-grain weight is 20 g or under 20 g, and the appearance is shown in the right part of the upper part of FIG. 2.

The receptor parent can be three-line maintainer line, or two-line GMS line or other types of CMS line hybrid rice, which all can be taken as female parent and hybridized with donor parent ZH-sg, and grains produced by first-filial generation hybrid plants are similar to the receptor parent. A quarter of individuals carrying sg gene are separated from F2' generation, and because genes of the receptor and the donor are recombined after hybridization, if the later generation is hoped to be similar to the receptor parent as much as possible, the receptor gene background selection can be carried out for the individuals carrying sg gene by means of molecular marker technology, which can improve the selection efficiency. If the later generation is hoped to maintain sg gene and be similar to the receptor parent in genotype as much as possible, the individuals carrying sg gene can be selected to backcross with the receptor parent 1-2 times or 3-5 times, so that the genotype of the later generation can return to the receptor parent rapidly.

When the separated later generation carries sg gene, it is should be noted that the type having larger ears than the receptor parent is selected to compensate the decrease of grain weight of the maintainer line (CMS line) or GMS line by increasing the number of grains per ear, thereby balancing or keeping original potential of yield.

Embodiment 2-1

Seed Production of Small Grain CMS Or GMS Line Hybrid Rice

When small grain CMS or GMS line hybrid rice is hybridized with large or normal grain restorer line hybrid rice for seed production, (1) if the difference between growth periods of the CMS or GMS line (with shorter growth period) and the restorer line (with longer growth period) is 10 days or more, the present production mode of hybrid rice seed production (transplanting restorer line male parent and CMS or GMS line female parent one after another) is stilled be used, and there is no need to separately harvest the male parent after the completion of flowering of the male parent (restorer line) and the female parent (CMS or GMS line), which is replaced by mixed harvesting with a reaper.

Embodiment 2-2

Seed Production of Small Grain CMS Or GMS Line Hybrid Rice

When small grain CMS or GMS line hybrid rice is hybridized with large or normal grain restorer line hybrid rice for seed production, (1) if the difference between growth periods of the CMS or GMS line (with shorter growth period) and the restorer line (with longer growth period) is less than 10 days, mixed sowing can be used in the way of not accelerating germination of the CMS or GMS line and accelerating germination of the restorer line, or mixed sowing or mixed transplanting is carried out directly. There is no need to separately harvest the male parent after the completion of flowering of the male parent (restorer line) and the female parent (CMS or GMS line), which is replace by mixed harvesting with a reaper.

Embodiment 3

Cleaning And Separation of Small Grain CMS Or GMS Line Hybrid Rice

Figures 1, 3:
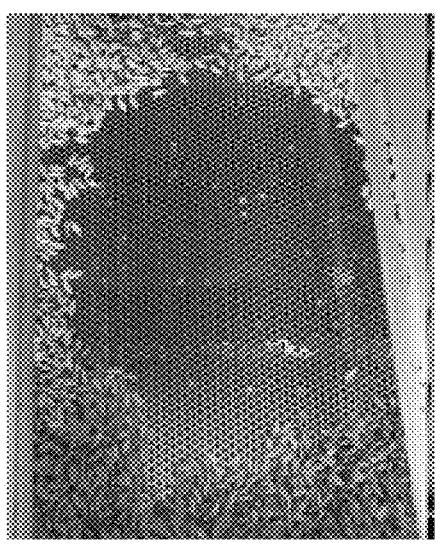
Figures 2, 3:
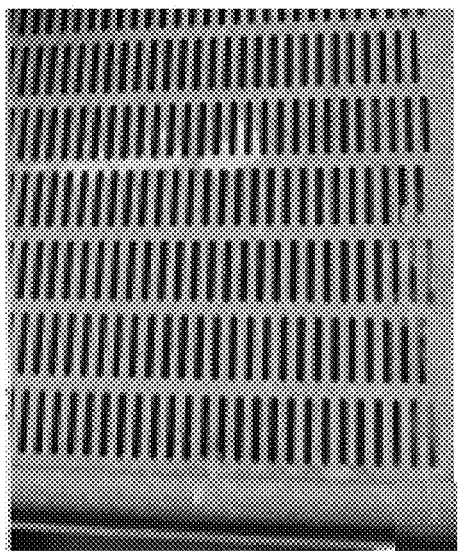

The harvested seeds are treated in the present dewatering mode of hybrid rice, and when the water content of the seeds meets the requirement, as shown in FIG. 3-2, a mesh screen with proper meshes according to the width of seeds of the CMS or GMS line is selected and mounted on a seed cleaner by selecting. On the basis of the principle that small grains of the CMS or GMS line (F1) can pass through meshes, and large grains of the restorer line can not pass through the meshes, the qualified dewatered seeds (CMS line and restorer line) are put into the seed cleaner for separation hybrid F1 from the male parent (restorer line).

Although the present invention has been described in detail and cites embodiments, various changes and/or supplements or replacements in similar modes for the embodiments will become apparent to those of ordinary skill in the art.

The invention claimed is:

1. A method for simplifying hybrid rice seed production procedure and improving the working efficiency of seed production, comprising the following steps:
   breeding providing a donor parent line, wherein the donor parent line is a small grain rice (*Oryza sativa*) ZH-sg (Zhonghua 11 small grain mutant) deposited under CGMCC No. 2741;
   providing a receptor parent line, wherein the receptor parent line is a male sterile line hybrid rice;
   hybridizing the donor parent line and the receptor parent line to obtain a F1 generation rice;
   hybridizing the F1 generation rice to obtain a F2 generation rice;
   selecting a small grain CMS or GMS line hybrid rice carrying ZH-sg from the F2 generation line;
   and hybridizing the small grain CMS or GMS line hybrid rice with a large grain or normal grain restorer line hybrid rice for seed producing.

2. The method according to claim 1, wherein the receptor parent line is selected from a three-line CMS maintainer line hybrid rice, and a two-line GMS line hybrid rice.

3. The method according to claim 1, wherein a 1000-grain weight of said small grain CMS or GMS line hybrid rice is 19-21 g or lighter than that of a large grain or normal grain CMS or GMS line hybrid rice by 25-45 percent.

4. The method according to claim 1, further comprising:
   at least one backcrossing to backcross the small grain CMS or GMS line hybrid rice with the receptor parent line to obtain a successive generation line rice; and
   selecting individual grains carrying ZH-sg gene from the successive generation line rice, wherein, the individual grains of the successive generation line rice undergo a receptor gene background selection by a molecular marker technology.

5. The method according to claim 1,
   wherein when a difference between a growth period of the small grain CMS or GMS line hybrid rice and a growth period of the restorer line hybrid rice is smaller than 10 days, the small grain CMS or GMS line hybrid rice and the restorer line hybrid rice are sown one after another or simultaneously sown together, and
   the restorer line hybrid rice is firstly transplanted and then the CMS or GMS line hybrid rice is directly sown or both of the small grain CMS or GMS line hybrid rice and the restore line hybrid rice are transplanted together.

6. The method according to claim 1, wherein when a difference between growth period of the small grain CMS or GMS line hybrid rice and a growth period of the restorer line hybrid rice is shorter than 10 days, both of the small grain CMS or GMS line hybrid rice and the restorer line hybrid rice are simultaneously sown together and transplanted together.

7. The method according to claim 1, further comprising sowing the restorer line, wherein the sowing of said restorer line hybrid rice includes mixing sowing or direct sowing when the restorer line hybrid rice has a 1000-grain weight larger than 26 g.

8. The method according to claim 1, further comprising:
   when hybrid seeds produced by hybridizing the small grain CMS or GMS line hybrid rice with the large grain or normal grain restorer line hybrid rice are fully grown, harvesting the hybrid seeds and the restorer line seeds together; and
   separating the hybrid seeds and the restorer line seeds by size.

9. The method according to claim 8, wherein separating the hybrid seeds from the restorer line seeds by size is carried out via a proper mesh screen.

10. The method according to claim 2, wherein a 1000-grain weight of said small grain CMS or GMS line hybrid rice is 19-21 g or lighter than that of a large grain or normal grain CMS or GMS line hybrid rice by 25-45 percent.

11. The method according to claim 5, wherein when a difference between a growth period of the small grain CMS or GMS line hybrid rice and a growth period of the restorer line hybrid rice is shorter than 10 days, both of the small grain CMS or GMS line hybrid rice and the restorer line hybrid rice are simultaneously sown together and transplanted together.

* * * * *